United States Patent [19]

Shasuzzaman et al.

[11] Patent Number: 4,526,868
[45] Date of Patent: Jul. 2, 1985

[54] RENNET SUBSTITUTE FROM SEALS FOR MAKING CHEESE

[76] Inventors: Kazi M. Shasuzzaman, 74 Fox Ave., St. John's, Newfoundland, Canada, A1B 2J2; Norman F. Haard, Marine Dr., Outer Cove, Newfoundland, Canada

[21] Appl. No.: 433,936

[22] Filed: Oct. 12, 1982

[30] Foreign Application Priority Data

Oct. 22, 1981 [CH] Switzerland ............................ 388552

[51] Int. Cl.³ ........................ C12N 9/64; A23C 19/04
[52] U.S. Cl. ..................................... 435/226; 426/36; 426/63; 435/814
[58] Field of Search .................. 435/226, 814; 426/63, 426/36

[56] References Cited

U.S. PATENT DOCUMENTS 3,281,332 10/1966 Munns et al. ........................ 435/226
4,081,330 3/1978 Horisberger et al. ............ 426/63 X

OTHER PUBLICATIONS

Davis, J. G., Cheese vol. I American Elserier Publishing Co., Inc. N.Y. 1965 (pp. 270–273).

Primary Examiner—David M. Naff
Attorney, Agent, or Firm—Millen & White

[57] ABSTRACT

A high potency calf rennet substitute having four proteolytic enzyme components is extracted from the stomach mucosa or whole stomach of seals. The substitute closely matches the characteristics of calf rennet by having good milk clotting efficiency over a wide range of pH of 6.0 to 6.8, a high ratio of milk clotting to proteolytic activity, relative inability to inactivate ribonuclease and limited hydrolysis of casein. The substitute results in a desirable aged flavor in cheddar cheese.

11 Claims, 6 Drawing Figures

RENNET SUBSTITUTE FROM SEALS FOR MAKING CHEESE

BACKGROUND OF THE INVENTION (i) Field of the Invention

This invention relates to a milk coagulating enzyme for the making of cheese, and to a method for its extraction.

(ii) Description of the Prior Art

Rennet, the traditional milk coagulating enzyme used for manufacturing cheese, is obtained from calf stomach, which at present is of limited supply. Therefore rennet is very costly. Consequently, milk coagulating enzymes from swine, chicken and adult bovine stomachs and also those from bacteria and fungi are used as rennet substitutes.

Rennet from calf stomachs have some unique characteristics which are missing in the substitutes. Consequently there are reports (e.g. in chapter 12 entitled "Milk Clotting Enzymes and Cheese Chemistry, Part 1. Milk-Clotting Enzymes and their Action, by C. A. Ernstrom et al in "Fundamentals of Dairy Chemistry" Second Edition, the Avi Publishing Company Inc. Westport Conn. 1974) that use of these substitutes results in cheeses of inferior quality and poorer yield. Thus, it was reported that most plant proteases are strongly proteolytic and cause extensive digestion of the curd. This has resulted in reduced yields, bitter flavors and pasty-bodied cheese. Patents have been issued for the production of and use of milk-clotting enzymes from bacteria, e.g. Godo Shusei Co., Japanese Pat. Nos. 27,714.69 (1969) and 12,225/70 (1970) and British Pat. Nos. 1156387 and 1156388 (1969); John Labatt Ltd., British Pat. Nos. 1,202,378 (1970), 1203371 (1970) and 1223860 (1971); and Murray et al, U.S. Pat. No. 3,543,563 (1970) and 3,507,750 (1970). However, results have not been consistently favorable. Patents have also been issued for the production of milk-clotting enzymes from fungi, e.g. Arima et al, U.S. Pat. No. 3,212,905 (1965), and W. German patent application No. 1,442,118 (1969); Aunstrup, W. German patent application No. 151,775 (1970); Charles et al, U.S. Pat. No. 3,549,390 (1970) and W. German patent application No. 1945447 (1970); and Sardinas, U.S. Pat. No. 3,275,453 (1966) and W. German patent application No. 1,442,140 (1968). In addition porcine pepsin and bovine pepsin have been investigated for their milk-clotting potential. For harder varieties of cheese, e.g., cheddar, which is the most popular in North America, these substitutes often need to be blended with calf rennet. Therefore, there is still considerable demand for a milk-clotting enzyme with characteristics closely resembling those of calf rennet.

SUMMARY OF THE INVENTION (i) Aims of the Invention

Accordingly, it is an object of this invention to provide a naturally-occurring substitute for rennet in cheese making.

Another object of this invention is to provide a method for producing such extract.

(ii) Statements of the Invention

By this invention, an extract has been provided from seal stomach which is a substitute for rennet as a milk coagulating enzyme for making cheese.

Thus, the present invention provides a high potency calf rennet substitute preparation having enzymes extracted from the mucosa of the stomach of seals or from the entire stomach of seals such preparation comprises four seal proteolytic enzyme components having a good milk clotting efficiency over a wide pH range of milk of 6.0 to 6.8, a high ratio of milk-clotting to proteolytic activity, relative inability to inactivate ribonuclease and limited hydrolysis of casein, the substitute having a potency of up to 80 rennin units per milliliter of extract when tested in reconstituted skim milk at pH 6.3 at 30° C. and the four proteolytic enzyme components having four isoelectric points at 4.9, 4.3, 3.8 and 3.4.

The present invention also provides a method for extracting a high potency calf rennet substitute preparation from seals comprising: homogenizing either the mucosa of the stomach of a seal, or the whole stomach of a seal with phosphate buffer; centrifuging the slurry and recovering the supernatant; activating the supernatant by adding hydrochloric acid thereto; and recovering the activated rennet substitute comprising seal proteolytic enzyme components and having four isoelectric points at 4.9, 4.3, 3.8 and 3.4 and having a good milk clotting efficiency over a wide pH range of milk of 6.0 to 6.8, a high ratio of milk clotting to proteolytic activity, relative inability to inactive ribonuclease and limited hydrolysis of casein, and, having a potency of up to 80 rennin units per milliliter of extract when tested in reconstituted skim milk at pH 6.3 at 30° C.

(iii) Other Features of the Invention

By a feature of this invention, the calf rennet substitute has a pH optimum of 2.6 for hemoglobin hydrolysis at 30° C.

By still another feature of this invention the two major seal proteolytic enzyme components have molecular weights of 28,500 and 40,000 daltons (as determined by gel filtration on SEPHADEX G-100), and the other two seal proteolytic enzyme components have molecular weights of 26,000 and 36,000 daltons respectively (also as determined by gel filtration on SEPHADEX G-100).

By yet a further feature of this invention, the two major seal proteolytic enzyme components have molecular weights of 40,000 and 50,000 Daltons by polyacrylamide, as determined by gel electrophoresis in the presence of sodium dodecyl sulphate, and the other two seal proteolytic enzyme components have molecular weights of 32,000 and 40,000 daltons, respectively (also as determined by polyacrylamide gel electrophoresis in the presence of sodium dodecyl sulphate).

By yet another feature of the method of this invention, the mucosa of the stomach of the seal is used and is a freeze-dried mucosa.

By another feature of this invention the buffer is used in an amount of 4 times the volume of the mucosa of the stomach of the seal or of the whole stomach of the seal, the phosphate buffer having a concentration of 0.02M and having a pH of 7.2, the buffer further containing penicillin, in an amount of 4 mg/l and streptomycin, in an amount of 50 mg/l.

By a further feature of this invention, the slurry is centrifuged at a speed of 20,000 r.p.m. at a temperature of 2°–5° C.

By yet another feature of this invention, the activating step comprises adding hydrochloric acid to the slurry until the pH is 2.0; and then allowing the acidified supernatant to stand at ambient temperature for one hour.

(iv) Generalized Description of the Invention

The crude preparation seal proteloytic enzyme precursors is composed of 4 components the major two of which have molecular weights of 28,500 and 40,000 daltons as determined by gel filtration on SEPHADEX G-100 (Trade Mark) column or 40,000 and 50,000 daltons by polyacrylamide gel electrophoresis in the presence of sodium dodecyl sulphate. The other two components have molecular weights of 26,000 and 36,000 daltons, respectively, as determined by gel filtration on SEPHADEX G-100 or have molecular weights of 32,000 and 40,000 daltons, respectively, as determined by polyacrylamide gel electrophoresis in the presence of sodium dodecyl sulphate. The crude active preparation has a pH optimum of 2.6 for hemoglobin hydrolysis at 30° C. Results of an isoelectric point determination revealed that the four components of the active preparation have isoelectric points of 4.9, 4.3, 3.8 and 3.4.

It has been found that such extract closely matches the characteristics of the calf rennet, namely, (1) it coagulates milk over a wide pH range from 6.0 to 6.8, (2) it has a high ratio of milk clotting to proteolytic activity, (3) it has limited action on milk proteins, (4) it has limited substrate specificity as evidenced by its relative inability to inactivate ribonuclease—a test used to distinguish rennin from other proteolytic enzymes; and (5) it results in a desirable aged flavor in cheddar cheese. Since pepsin (3.4.4.1) inactivates ribonuclease (2.7.7.16) by splitting off a tetrapeptide from the C-terminus, and since rennet has no effect on ribonuclease, rennin can be distinguished from pepsin by this test.

It has also been found that such extract has an additional advantage in that unlike milk coagulating enzymes from ruminant stomachs, proteotytic enzyme pattern in seal stomachs does not change drastically with age and diet. Proteotytic enzymes from bovine stomachs, for example, contain pepsin in addition to rennin and the proportion of the former increases with advancing age and diet of the animal to the extent that at the age of 5 months rennin in calf stomach is almost completely replaced by pepsin. Bovine, porcine and chicken pepsins are inferior to rennin for making cheddar cheese.

The procedure for preparing such extract according to an aspect of this invention is much simpler than that used for microbial rennets which involves the use of complex growth media and sophisticated equipment. Besides, since seal stomachs are now a wasted by-product of the sealing industry, it should be available relatively cheaply.

One method of extraction is as follows: Fresh or frozen and thawed stomach is dissected to obtain the mucosa, or the whole stomach after cleaning can be used. The mucosa or the stomach is then freeze-dried or processed. To prepare the extract, the freeze-dried stomach is homogenized using 4 volumes of 0.02M phosphate buffer, pH 7.2. The slurry thus obtained is centrifuged at 20,000 r.p.m. at 2°–5° C. The clear supernatant contains the precursor of the seal rennet. To activate it, the preparation is dialysed and hydrochloric acid is added with stirring until the pH is 2.0 and left at ambient temperature for an hour. The potency of the preparation is up to 80 rennin units per milliliter of extract when tested in reconstituted skim milk at pH 6.3 at 30° C. One rennin unit is the potency that clots 10 ml of reconstituted milk in 100 seconds under these conditions.

The potency of the seal rennet in Soxhlet was calculated using an appropriate equation that appears in U.S. Pat. No. 3,549,390 an appropriate equation that appears in U.S. Pat. No. 3,549,390 following the milk coagulation method described therein with slight modification. The volumes of milk and rennet were scaled down to 1.0 ml and 0.01 ml respectively after proper dilution of the enzyme. One ml of rennet preparation from seal stomach was found to have a potency of up to 5,000 Soxhlet units.

The maximum potency of this extract is only slightly lower than the reported value of rennin preparations from calf stomach (see, for example ACTA CHEMICA SCANDINAVICA 13 (1959) 1927–1935, entitled "Studies on Rennin 11. On the Crystallization, Stability and Proteolytic Activity of Rennin" by Bent Foltmann) and some microbial rennet preparations, (see U.S. Pat. No. 3,661,594 issued May 9, 1972 to T. Imae et al and U.S. Pat. No. 3,607,655 issued Sept. 21, 1971 to N. Mukai et al.).

(E) BRIEF DESCRIPTION OF THE DRAWINGS

In the accompanying drawings.

(F) DESCRIPTION OF PREFERRED EMBODIMENTS

Figure 1B:
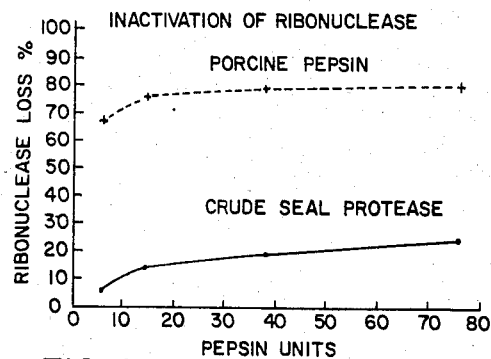
FIGS. 1A and 1B are graphs of the inactivation of ribonuclease, with % loss of ribonuclease as ordinate and pepsin units as abscissa for porcine pepsin and seal protease.
Figure 1A:
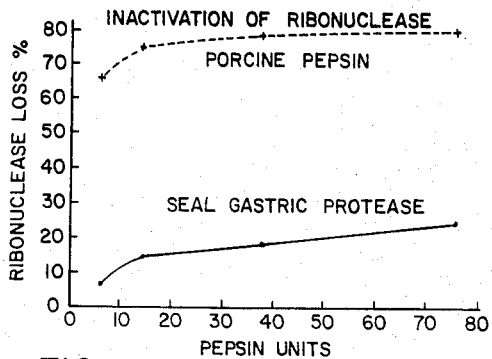

The action of rennets on ribonuclease was determined by the following method:

Inactivation of bovine pancreatic ribonuclease by seal proteolytic enzymes and porcine pepsin was compared. The method of Berger et al. (see Biochem Biophys. Acta, 33, 249 (1954), A Berger et al.) was followed except for seal protease which was incubated at its pH optimum of 2.6. Bovine ribonuclease was dissolved in 0.01N HCl for reaction with porcine pepsin and in 50 mM citrate solution pH adjusted to 3.4 so that the final pH would be 2.6. The concentration of the ribonuclease was 3 mg/ml. To 0.25 ml of this solution was added 0.1 ml solution of active seal enzymes or porcine pepsin containing 0 to 76.2 pepsin units of the respective enzyme based on hemoglobin hydrolysis. This mixture was incubated in a water bath held at 30° C. After 40 minutes the reaction was stopped by the addition of 0.25 ml of 1.5M solution of $NaH_3PO_4$ pH adjusted to 7.0. To this was added 14 ml water. After shaking, 0.1 ml aliquot of this mixture was pipetted into a test tube containing 0.65 ml of 0.1M sodium acetate pH 5.0 and 1.0 ml of a solution of 1% ribonucleic acid in 0.1 M acetate pH 5.0. After mixing the test tubes were incubated at 25° C. in a water bath for 24 minutes. The reaction was then stopped by adding 0.25 ml solution of 0.75% uranylacetate in 24% perchloric acid. After centrifugation 30 microliters of the clear supernatant was diluted with 1 ml of water and its absorbance measured at 260 nm in a Beckman model DU8 spectrophotometer. In this experiment it was found that the extent of inactivation of ribonuclease by seal crude protease was much less than that by equal potencies of porcine pepsin. For example, as seen in FIGS. 1A and 1B, 7.6 pepsin units of swine pepsin inactivated 66% of the ribonuclease whereas seal enzyme with the same potency inactivated only 6% of the ribonuclease in the same period of reaction.

The time course of casein hydrolysis was followed by the following method (See R. G. Wake, (1959) Aust. J. Biol. Sci. 12, 497):

Forty milliliters of a 2% solution of casein, pH adjusted to 6.1 was equilibrated at 30° C. in a water bath. To this was added 0.2 ml solution containing either crude seal stomach enzyme obtained from a 2 year old harp seal or porcine pepsin. The amount of enzyme was adjusted so that it would clot 40 ml of milk in 20 minutes at 30° C. The mixture was shaken. Immediately after adding the enzyme and at various time intervals thereafter 2 ml aliquots of the mixture were withdrawn and mixed with 2 ml of a 24% solution of trichloroacetic acid (TCA). After cooling for 30 minutes at 4° C. the precipitated samples were centrifuged at 3000 xg and the supernatants thus obtained were subjected to nitrogen determination following the method of Lang. ("Simple Microdetermination of Kjeldahl Nitrogen in Biological Materials", A. Cary, Vol. 30 No. 10 Act 1953).

Figure 2A:
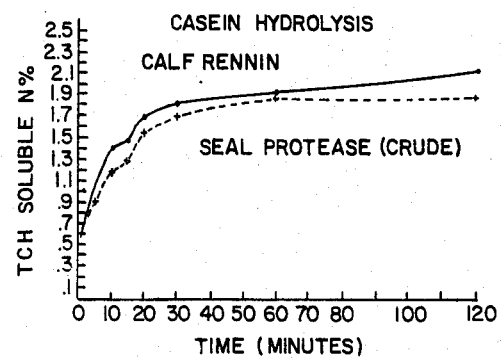
FIGS. 2A–2C are graphs of casein hydrolysis with TCA soluble nitrogen as ordinate and time in minutes as abscissa for calf rennin, seal protease and porcine pepsin.
Figure 2B:
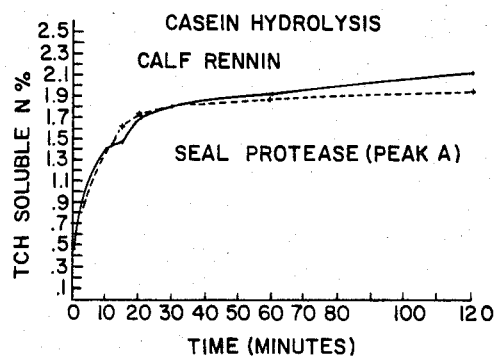
Figure 2C:
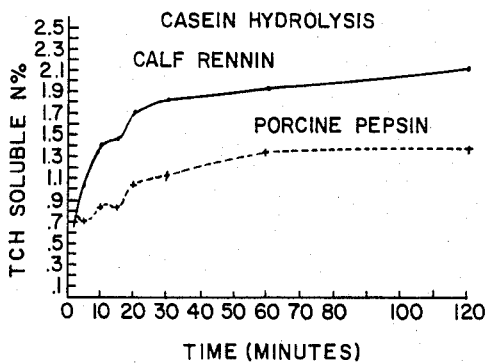

As shown in FIGS. 2A–2C, the results show that the amount of TCA soluble nitrogen released by seal protease was 1.8% in 60 minutes and there was no further release upon an additional incubation for 60 minutes. In the case of calf rennin the release of TCA soluble nitrogen was slightly higher. The significance of these results is that under these conditions, seal proteases, (like rennin) effect limited hydrolysis of milk proteins which is a desirable characteristic because further hydrolysis beyond what is required for milk coagulation may result in lower yield of cheese.

Figure 3:
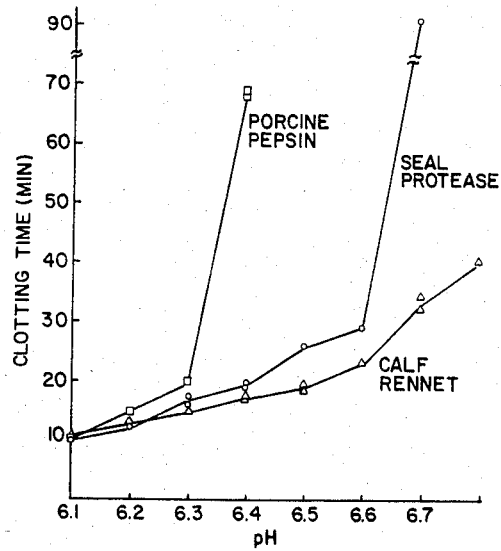
FIG. 3 is a graph of clotting time in minutes as ordinate and pH as abscissa for porcine pepsin, seal protease and calf rennet.

The milk clotting activity of the extract with respect to pH was determined as follows: Twelve grams of skim milk powder (that known by the Trade Mark CARNATION) were mixed into a homogeneous suspension in 100 ml of 0.01M $CaCl_2$ solution. Aliquots of this suspension were adjusted to pH 6.1 to 6.8 by small additions of either 1M HCl or 1M NaOH. One milliliter volumes of these samples were then incubated with 50 microliters of seal enzyme, swine pensin or calf rennin and the mixture incubated in a water bath set at 37° C. The concentration of the enzymes were so adjusted that they will clot the milk at pH 6.1 in approximately equal time (10 min±15 seconds). The results are shown in FIG. 3. It can be seen that seal enzyme preparation had milk clotting times close to those of calf rennet up to 6.6 whereas swine pepsin took much longer to clot milk at pH 6.3 and beyond.

The seal gastric extract of one aspect of this invention may thus be characterized by the following parameters.

The crude preparation of seal proteolytic enzyme precursors is composed of 4 components the major two of which have molecular weights of 28,500 and 40,000 daltons as determined by gel filtration on a SEPHADEX G-100 (Trade Mark) column and 40,000 and 50,000 daltons by polyacrylamide gel electrophoresis in the presence of sodium docecyl sulphate. The crude preparation has a pH optimum of 2.6 for hemoglobin hydrolysis at 30° C. Results of an isoelectric point determination revealed that the four components of the active preparation have isoelectric points of 4.9, 4.3, 3.8 and 3.4.

A simple method of extraction of a high potency rennet substitute has been described. This is the only animal rennet preparation from a novel source with characteristics similar to those of traditional calf rennet, namely, good clotting efficiency over a wide pH range of milk, relative inability to inactivate ribonuclease (a definitive test for a true rennet) and limited hydrolysis of casein.

The preparation obtained had higher range of milk clotting efficiency than the reported values of those obtained from calf stomach, and some of the patented substitutes of microbial origin.

The seal rennet was found to be equally efficient as commercial calf rennet in a small scale cheddar cheese preparation.

Cheddar cheese was prepared from 18 L milk using crude and semipurified seal enzymes, calf rennet and also a commercial fungal rennet. The cheeses were vacuum packed and cured at 8° C. for 7 months after which they were evaluated by a taste panel comprising 30 experienced tasters. They were asked to evaluate the cheeses on a nine point hedonic scale, e.g. 1 for extremely disliking and 9 for extremely liking a particular cheese. The results showed that the cheese prepared by using crude seal enzyme had a significantly higher sensory score than the other cheeses including the one prepared using rennet whereas there was no significant difference in scores between rennet cheese and the fungal rennet and the semipurified seal enzyme cheese. Results are tabulated below in Table I.

| | SENSORY EVALUATION OF CHEDDAR CHEESES AFTER 7 MONTHS OF CURING | | | |
|---|---|---|---|---|
| | CHEESE PREPARED USING | | | |
| JUDGE NUMBER | semi purified seal rennet | control rennet | fungal rennet | crude seal rennet |
| | sensory score | | | |
| 1 | 5 | 5 | 6 | 6 |
| 2 | 7 | 6 | 7 | 9 |
| 3 | 8 | 8 | 8 | 8 |
| 4 | 8 | 9 | 8 | 6 |
| 5 | 3 | 7 | 2 | 7 |
| 6 | 4 | 8 | 6 | 3 |
| 7 | 7 | 3 | 6 | 8 |
| 8 | 2 | 7 | 6 | 9 |
| 9 | 6 | 4 | 6 | 8 |
| 10 | 6 | 6 | 5 | 7 |
| 11 | 5 | 3 | 4 | 9 |
| 12 | 5 | 2 | 5 | 7 |
| 13 | 4 | 8 | 6 | 7 |
| 14 | 5 | 2 | 6 | 8 |
| 15 | 6 | 6 | 4 | 7 |
| 16 | 8 | 5 | 5 | 5 |
| 17 | 7 | 4 | 8 | 9 |
| 18 | 3 | 3 | 2 | 7 |
| 19 | 8 | 6 | 7 | 5 |
| 20 | 5 | 6 | 7 | 4 |
| 21 | 6 | 7 | 7 | 8 |
| 22 | 4 | 7 | 6 | 3 |
| 23 | 7 | 8 | 7 | 8 |
| 24 | 6 | 5 | 5 | 7 |
| 25 | 8 | 4 | 7 | 7 |
| 26 | 7 | 7 | 7 | 6 |
| 27 | 6 | 7 | 5 | 8 |
| 28 | 7 | 7 | 7 | 7 |
| 29 | 5 | 3 | 5 | 5 |
| 30 | 7 | 7 | 7 | 7 |
| mean | 5.83 ± 1.64 | 5.67 ± 1.97 | 5.90 ± 1.52 | 6.83 ± 1.64 |
| Liked by | 18 Judges | 18 Judges | 20 Judges | 24 Judges |
| Neither like/ Disliked by | 6 Judges | 3 Judges | 6 Judges | 3 Judges |

| | SENSORY EVALUATION OF CHEDDAR CHEESES AFTER 7 MONTHS OF CURING -continued | | | |
|---|---|---|---|---|
| | CHEESE PREPARED USING | | | |
| JUDGE NUMBER | semi purified seal rennet | control rennet | fungal rennet | crude seal rennet |
| Disliked by | 6 Judges | 9 Judges | 4 Judges | 3 Judges |

(G) SUMMARY

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What we claim is:

1. A high potency calf rennet substitute preparation having enzymes extracted from the mucosa of the stomach of seals or from the whole stomach of seals comprising four seal calf rennet substitute, said proteolytic enzyme components having a good milk clotting efficiency over a wide range of pH of 6.0 to 6.8, a high ratio of milk clotting to proteolytic activity, relative inability to inactivate ribonuclease and limited hydrolysis of casein, and having a potency of up to 80 rennin units per millimeter thereof when tested in reconstituted skim milk at a pH 6.3 at 30° C., said four, proteolytic enzyme components having four isoelectric points at 4.9, 4,3, 3.8 and 3.4.

2. The calf rennet substitute of claim 1 having a pH optimum of 2.6 for hemoglobin hydrolysis at 30° C.

3. The calf rennet substitute of claim 1 wherein the major two of said seal proteolytic enzyme components have molecular weights of 28,500 and 40,000 daltons respectively, as determined by gel filtration on SEPHADEX G-100.

4. The calf rennet substitute of claim 1 wherein the major two of said seal proteolytic enzyme components have molecular weights of 40,000 and 50,000 daltons respectively, as determined by polyacrylamide gel electrophoresis in the presence of sodium dodecyl sulphate.

5. The calf rennet substitute of claim 3 wherein the other two of said proteolytic seal enzyme components have molecular weights of 26,000 and 36,000 daltons, respectively, as determined by gel filtration on SPEHADEX G-1000.

6. The calf rennet substitute of claim 4 wherein the other two of said seal proteolytic enzyme components have molecular weights of about 32,000 and 40,000 daltons, respectively, as determined by polyacrylamide gel electrophoresis in the presence of sodium dodecyl sulphate.

7. A method for extracting a high potency calf rennet substitute preparation from seals comprising: homogenizing at least one of the mucosa of the stomach of a seal or the whole stomach of a seal with a phosphate buffer; centrifuging the slurry so formed and recovering the supernatant therefrom; activating said supernatant by adding hydrochloric acid thereto; and recovering an activated rennet substitute, said substitute comprising four seal proteolytic enzyme components and having four isoelectric points at 4.9, 4.3, 3.8 and 3.4 and also having a good milk clotting efficiency over a wide pH range of milk of 6.0 to 6.8, a high ratio of milk clotting to proteolytic activity, relative inability to inactivate ribonuclease and limited hydrolysis of casein, and a potency of up to 80 rennin units per milliliter thereof when tested in reconstituted skim milk at a pH of 6.3 at 30° C.

8. The method of claim 1 wherein the mucosa is used and is freeze-dried mucosa.

9. The method of claim 7 wherein said phosphate buffer is used in an amount of 4 times the volume of said mucosa of said stomach or of the whole said stomach, said phosphate buffer having a concentration of 0.02M and having a pH of 7.2, said buffer containing penicillin, in an amount of 4 mg/l, and streptomycin in an amount of 50 mg/l.

10. The method of claim 7 wherein said slurry is centrifuged at a speed of 20,000 r.p.m. at a temperature of 2°–5° C.

11. The method of claim 7 wherein said activating step comprises adding hydrochloric acid to said slurry until the pH is 2.0; and then allowing said acidified supernatent to stand at ambient temperature for one hour.

* * * * *

UNITED STATES PATENT AND TRADEMARK OFFICE
CERTIFICATE OF CORRECTION

PATENT NO. : 4,526,868
DATED : July 2, 1985
INVENTOR(S) : KAZI M. SHAMSUZZAMAN ET AL It is certified that error appears in the above-identified patent and that said Letters Patent is hereby corrected as shown below:

Title page, first inventor: reads "Kazi M. Shasuzzaman"

should read --Kazi M. Shamsuzzaman--

Signed and Sealed this

Twenty-fourth Day of December 1985

[SEAL]

Attest:

DONALD J. QUIGG

Attesting Officer

Commissioner of Patents and Trademarks